United States Patent [19]

Bulford et al.

[11] 4,157,356

[45] Jun. 5, 1979

[54] PROCESS FOR AROMATIZING $C_3$-$C_8$ HYDROCARBON FEEDSTOCKS USING A GALLIUM CONTAINING CATALYST SUPPORTED ON CERTAIN SILICAS

[75] Inventors: Stanley N. Bulford, Shepperton; Evan E. Davies, Woking, both of England

[73] Assignee: The British Petroleum Company Limited, London, England

[21] Appl. No.: 856,667

[22] Filed: Dec. 2, 1977

[30] Foreign Application Priority Data

Dec. 20, 1976 [GB] United Kingdom ............... 53011/76

[51] Int. Cl.$^2$ ........................ C07C 15/02; B01J 23/08
[52] U.S. Cl. ................................ 585/415; 208/136; 208/138; 252/453; 252/455 R; 252/477 R
[58] Field of Search ............................ 260/673, 673.5; 252/453, 455 R

[56] References Cited

U.S. PATENT DOCUMENTS

| | | | |
|---|---|---|---|
| 3,770,616 | 11/1973 | Kominami et al. | 208/138 |
| 3,926,781 | 12/1975 | Gale | 208/117 |
| 4,048,249 | 9/1977 | Antos | 260/673.5 |
| 4,056,575 | 11/1977 | Gregory et al. | 260/673.5 |
| 4,056,576 | 11/1977 | Gregory et al. | 260/683.3 |

*Primary Examiner*—Delbert E. Gantz
*Assistant Examiner*—G. E. Schmitkons
*Attorney, Agent, or Firm*—Brooks, Haidt, Haffner & Delahunty

[57] ABSTRACT

This case relates to a process for producing aromatic hydrocarbons by contacting a $C_3$-$C_8$ hydrocarbon with a gallium catalyst on a silica support which has a surface area greater than 500 m$^2$/g and a pore volume less than 0.8 ml/g.

16 Claims, No Drawings

PROCESS FOR AROMATIZING C₃–C₈ HYDROCARBON FEEDSTOCKS USING A GALLIUM CONTAINING CATALYST SUPPORTED ON CERTAIN SILICAS

The present invention relates to a process for dehydrocyclodimerisation of $C_3$–$C_8$ hydrocarbon feedstock to aromatic hydrocarbons, especially xylenes.

It has been known to use chromium oxide and/or aluminas as catalysts in the production of aromatics from open chain hydrocarbons. However, such catalysts have a very short life and need frequent regenerations to maintain activity due to the severity of the reaction conditions needed to carry out the reaction.

Catalysts have now been found which when compared with conventional catalysts show significantly increased activity.

Accordingly, the present invention is a process for producing aromatic hydrocarbons comprising contacting at an elevated temperature a $C_3$–$C_8$ hydrocarbon feedstock with a catalyst composition comprising gallium on a silica support wherein the silica has a surface area of over 500 meter²/gram and a pore volume of less than 0.8 ml/gram.

By $C_3$–$C_8$ feedstock is meant here and throughout the specification a feedstock containing a single hydrocarbon component or mixtures of saturated and/or unsaturated $C_3$–$C_8$ hydrocarbons. $C_4$ feedstock containing isobutane and/or isobutene in the feedstock are particularly useful.

The silica support of the present invention has a surface area of over 500 meter²/gram, preferably between 600 and 800 meter²/gram. The pore volume of the silica support is preferably between 0.5 ml/gram and 0.05 ml/gram. It is also preferable that the mean pore diameter of the silicas is less than 65Å. The higher surface area and low pore volume can result in the use of a lesser amount of gallium than hitherto and it has also been found surprisingly that the smaller amount of gallium is more active. The silica supports suitably have surface hydroxyl groups available for exchange.

The gallium in the catalyst composition may be present as gallium oxide and or gallium ion depending upon whether the silica support has free hydroxyl groups available on the surface thereof for exchange.

If the silica support is free from surface hydroxyl groups, the gallium may be impregnated on the surface thereof as gallium oxide or as a gallium compound which gives rise to gallium oxide during activation of the catalyst prior to contact with the hydrocarbon feedstock. Examples of such gallium compounds include gallium nitrate, gallium sulphate and gallium chloride. Conventional impregnation techniques may be used to produce these catalysts.

If the silica support has surface hydroxyl groups available for exchange, gallium ions may be exchanged for the hydrogen in such surface hydroxyl groups on the silica support. The gallium ion may be provided by aqueous solutions of gallium salts such as for instance gallium nitrate, gallium chloride or gallium sulphate. Such catalysts may be produced by conventional ion exchange techniques and the catalysts so produced are subsequently dried.

Whichever method is used, the amount of gallium present in such catalyst compositions may vary for instance between 0.1 and 10%, preferably between 0.5 and 5% by weight of the total support in the catalyst composition.

The catalyst composition of the present invention may also contain other metals such as palladium, indium, germanium, chromium, tin and/or zinc in small quantities to improve the activity thereof.

The catalyst compositions of the present invention may be activated at an elevated temperature prior to contact with the hydrocarbon feedstock. The activation may be carried out by passing air, hydrogen or a gas inert under the reaction conditions such as nitrogen over the catalyst at or near the proposed reaction temperature preferably between 500° and 600° C. The activation may be carried out in the reactor tube itself. The catalyst composition is suitably used as a fixed bed.

The hydrocarbon feedstock as hereinbefore described is thereafter passed over the catalyst at an elevated temperature for instance between 450° and 700° C., preferably between 500° and 600° C. in an atmosphere which is inert under the reaction conditions, such as nitrogen. The products of the reaction are then isolated and identified.

The present invention is illustrated below with reference to the following Examples.

PREPARATION OF THE CATALYST

The catalyst was in all cases prepared by the following method using the relevant silica support:

4.5 grams of gallium nitrate, $Ga(NO_3)_3 \cdot 2H_2O$, was dissolved in 200 mls of distilled water. Ammonia solution was carefully added until the pH was adjusted to 2.5. 30 ml of the silica gel under test was packed into a glass column and the gallium nitrate solution was percolated through the column for 18 hours. The catalyst was finally washed with 1500 ml of distilled water and dried in a vacuum oven overnight. The gallium exchanged silica catalyst was heated in air at 600° C. for 18 hours overnight before use.

EXAMPLES 1-3

The results obtained when isobutane was passed over catalysts prepared as described above at atmospheric pressure and 600° C. are shown in Table 1.

TABLE 1

Aromatisation of isobutane at 600° C., 1 atmosphere pressure over a 15 ml charge of gallium exchanged silica catalysts at a contact time of 6 seconds.

|  | Comparative Test Silica X | Ex 1 Silica A | Ex 2 Silica B | Ex 3 Silica C |
|---|---|---|---|---|
| Surface Area meter² | 390 | 540 | 760 | 740 |
| Pore Volume ml/g | 0.91 | 0.76 | 0.39 | 0.43 |
| Mean Pore Diameter A | 95 | 60 | 20 | 25 |
| Gallium % wt | 1.0 | 1.9 | 0.8 | 1.0 |
| Conversion % wt | 0 | 63.9 | 73.2 | 78.4 |
| Total Aromatics % wt | 0 | 11.5 | 18.6 | 21.7 |
| Xylenes % wt | 0 | 7.4 | 12.0 | 14.0 |

It can be seen that catalyst supported by silicas A, B or C show a greater activity for aromatisation than catalysts supported by silica X of the comparative test.

EXAMPLES 4 AND 5

Gallium exchanged silicas were prepared as in Examples 1 to 3 but omitting pH adjustment by ammonia addition. Silica D was prepared from Silica B (Table 1) by standing under 4 liters of nitric acid for 6 hours.

After drying, the 15 ml charge of catalysts under test were heated at 600° C. for 18 hours in air. Isobutene was then introduced at 600° C., atmospheric pressure and with a contact time of 6 seconds. The results obtained are shown in Table 2.

TABLE 2

Aromatisation of isobutene at 600° C., 1 atmosphere pressure over gallium exchanged silica catalysts at a contact time of 6 seconds.

|  | Comparative Test Silica X | Ex 4 Silica A | Ex 5 Silica D |
|---|---|---|---|
| Surface Area meter$^2$/g | 390 | 540 | 603 |
| Pore Volume ml/g | 0.91 | 0.76 | 0.31 |
| Mean Pore Diameter A | 95 | 60 | 20 |
| Gallium | 1.0 | 0.56 | 0.24 |
| Conversion % wt | 76.3 | 81.6 | 83.6 |
| Total Aromatics % wt | 26.2 | 27.4 | 33.9 |
| Xylenes % wt | 19.0 | 20.7 | 22.4 |

It can be seen that the higher surface area-lower pore volume silicas A and D exchange the lower amount of gallium but nevertheless are more active for aromatisation than the lower surface area-higher pore volume Silica X.

We claim:

1. A process for producing aromatic hydrocarbons comprising contacting at an elevated temperature a $C_3$-$C_8$ hydrocarbon feedstock with a catalyst composition consisting essentially of gallium on a silica support wherein the silica has a surface area greater than 500 m$^2$/g and a pore volume of less than 0.8 ml/g.

2. A process according to claim 1 wherein the feedstock is a $C_4$ hydrocarbon containing isobutane and/or isobutene.

3. A process according to claim 1 wherein the silica support has a surface area between 600 and 800 m$^2$/g.

4. A process according to claim 1 wherein the silica support has a pore volume between 0.5 ml/g and 0.05 ml/g. and a mean pore diameter of the silica support is less than 65Å.

5. A process according to claim 1 wherein the catalyst composition is activated at a temperature between 500° and 600° C. by passing air, hydrogen or a gas inert under the reaction conditions prior to contact with the hydrocarbon feedstock.

6. A process according to claim 1 wherein gallium is impregnated on the silica support as gallium oxide or as a compound giving rise to gallium oxide during activation.

7. A process according to claim 1 wherein the silica support has surface hydroxyl groups available for exchange.

8. A process according to claim 7 wherein the catalyst composition is prepared by exchanging the surface hydroxyl groups of silica with gallium ions.

9. A process according to claim 1 wherein the catalyst composition contains between 0.1 and 10.0% by weight of gallium based on the total weight of the support.

10. A process according to claim 1 wherein the hydrocarbon feedstock is contacted with the catalyst composition at a temperature between 450° and 750° C.

11. A catalyst composition consisting essentially of gallium on a silica support wherein the silica has a surface area greater than 500 m$^2$/g and a pore volume of less than 0.8 ml/gram.

12. A catalyst composition as defined in claim 11 wherein said silica has a surface area of between about 600 to 800 m$^2$/g and a pore volume between about 0.5 ml/g and 0.05 ml/g and a mean pore diameter of less than 65 Å.

13. A catalyst composition as defined in claim 11 wherein gallium is impregnated on the silica support as gallium oxide or as a compound giving rise to gallium oxide during activation.

14. A catalyst composition as defined in claim 11 which additionally contains one or more of the metals palladium, indium, germanium, chromium, tin and zinc.

15. A catalyst composition as defined in claim 11 wherein said silica support has surface hydroxyl groups available for exchange.

16. A process as defined in claim 1 wherein said catalyst composition additionally contains one or more of the metals palladium, indium, germanium, chromium, tin, and zinc.

* * * * *